(12) United States Patent
Fukuoka et al.

(10) Patent No.: US 8,945,309 B2
(45) Date of Patent: Feb. 3, 2015

(54) CATALYST FOR CELLULOSE HYDROLYSIS AND/OR REDUCTION OF CELLULOSE HYDROLYSIS PRODUCTS AND METHOD OF PRODUCING SUGAR ALCOHOLS FROM CELLULOSE

(75) Inventors: Atsushi Fukuoka, Sapporo (JP); Paresh Laxmikant Dhepe, Sapporo (JP)

(73) Assignee: National University Corporation Hokkaido University, Sapporo-Shi, Hokkaido (JP)

( * ) Notice: Subject to any disclaimer, the term of this patent is extended or adjusted under 35 U.S.C. 154(b) by 70 days.

(21) Appl. No.: 12/224,433

(22) PCT Filed: Mar. 1, 2007

(86) PCT No.: PCT/JP2007/053935
§ 371 (c)(1),
(2), (4) Date: Jan. 7, 2009

(87) PCT Pub. No.: WO2007/100052
PCT Pub. Date: Sep. 7, 2007

(65) Prior Publication Data
US 2009/0217922 A1    Sep. 3, 2009

(30) Foreign Application Priority Data

Mar. 1, 2006   (JP) ................................ 2006-054342

(51) Int. Cl.
| | | |
|---|---|---|
| C08B 30/00 | (2006.01) |
| C08B 37/00 | (2006.01) |
| C13K 1/02 | (2006.01) |
| B01J 29/00 | (2006.01) |
| B01J 29/18 | (2006.01) |
| B01J 21/00 | (2006.01) |
| B01J 23/42 | (2006.01) |
| B01J 23/40 | (2006.01) |
| B01J 29/068 | (2006.01) |
| B01J 29/44 | (2006.01) |
| B01J 29/12 | (2006.01) |
| B01J 35/00 | (2006.01) |
| B01J 29/03 | (2006.01) |
| C07C 29/141 | (2006.01) |
| B01J 29/74 | (2006.01) |
| B01J 23/46 | (2006.01) |
| B01J 29/22 | (2006.01) |
| B01J 21/06 | (2006.01) |
| B01J 21/04 | (2006.01) |
| B01J 23/70 | (2006.01) |
| B01J 35/02 | (2006.01) |
| B01J 23/48 | (2006.01) |
| B01J 21/18 | (2006.01) |
| B01J 21/12 | (2006.01) |

(52) U.S. Cl.
CPC *B01J 23/42* (2013.01); *B01J 23/40* (2013.01); *B01J 21/063* (2013.01); *B01J 21/04* (2013.01); *B01J 23/70* (2013.01); *B01J 29/068* (2013.01); *B01J 29/44* (2013.01); *B01J 35/026* (2013.01); *B01J 23/48* (2013.01); *B01J 29/126* (2013.01); *B01J 21/066* (2013.01); *B01J 21/18* (2013.01); *B01J 35/0066* (2013.01); *B01J 29/0325* (2013.01); *C07C 29/141* (2013.01); *B01J 21/12* (2013.01); *B01J 29/7415* (2013.01); *B01J 23/462* (2013.01); *B01J 2229/18* (2013.01); *B01J 29/22* (2013.01)
USPC ................... 127/34; 127/36; 127/37; 502/74; 502/261; 502/262; 502/334

(58) Field of Classification Search
None
See application file for complete search history.

(56) References Cited

U.S. PATENT DOCUMENTS

| | | | | |
|---|---|---|---|---|
| 4,018,620 | A * | 4/1977 | Penque | 127/37 |
| 4,058,411 | A * | 11/1977 | Bellamy et al. | 127/37 |
| 4,396,786 | A * | 8/1983 | Bond et al. | 585/240 |
| 4,470,851 | A | 9/1984 | Paszner et al. | |
| 4,950,812 | A * | 8/1990 | Jacobs et al. | 568/863 |
| 5,107,018 | A | 4/1992 | Schuster | |
| 6,177,598 | B1 * | 1/2001 | Brunner et al. | 568/863 |
| 7,618,917 | B2 | 11/2009 | Vanoppen et al. | |
| 2004/0171889 | A1 | 9/2004 | Vanoppen et al. | |

(Continued)

FOREIGN PATENT DOCUMENTS

| | | |
|---|---|---|
| DE | 1 066 567 | 10/1959 |
| EP | 0 329 923 | 8/1989 |

(Continued)

OTHER PUBLICATIONS

N. Dechamp et al., Kinetics of glucose hydrogenation in a trickle-bed . . . , Catalysis Today, vol. 24, 1995, pp. 29-34.
B. Kusserow, Hydrogenation of Glucose to Sorbitol over Nickel and Ruthenium Catalysts, Advanced Synthesis and Catalysis, vol. 345, 2003, pp. 289-299.
P. Gallezot et al., Glucose Hydrogenation on Ruthenium Catalysts in a Trickle-bed Reactor, Journal of Catalysis, vol. 180, 1998, pp. 51-55.
B. W. Hoffer et al., Carbon supported ru catalysts as promising alternative for raney-type . . . , Catalysis Today, vol. 79-80, 2003, pp. 35-41.
A. Fukuoka, Catalytic Conversion of Cellulose into Sugar Alcohols, Angewandte Chemie Interantional Edition, vol. 45, No. 31, 2006, pp. 5161-5163.

(Continued)

*Primary Examiner* — Melvin C Mayes
*Assistant Examiner* — Michael Forrest
(74) *Attorney, Agent, or Firm* — Jacobson Holman Hershkovitz PLLC

(57) ABSTRACT

A catalyst for cellulose hydrolysis and/or the reduction of hydrolysis products, in which a transition metal of group 8 to 11 is supported on a solid support. A method of producing sugar alcohols comprising: hydrolyzing cellulose in the presence of the catalyst in a hydrogen-containing atmosphere with pressurization; and reducing the hydrolysis product of cellulose. Provided are a catalyst for use in the production of sugar alcohols by the hydrolysis and hydrogenation of cellulose that affords easy separation of catalyst and product, and that does not require pH adjustment, acid or alkali neutralization, or activation of the catalyst during reuse, and a method of producing sugar alcohols from cellulose employing this catalyst.

2 Claims, 7 Drawing Sheets

(56) References Cited

U.S. PATENT DOCUMENTS

2004/0176619 A1 9/2004 Vanoppen et al.
2008/0210222 A1 9/2008 Vanoppen et al.

FOREIGN PATENT DOCUMENTS

| JP | 62-277332 | 12/1987 |
|---|---|---|
| JP | 62-277332 A | 12/1987 |
| JP | 2004-532275 | 10/2004 |
| JP | 2004-532275 A | 10/2004 |
| RU | 2004100530 | 6/2005 |
| SU | 1701115 | 12/1991 |
| WO | WO 02/102939 | 12/2002 |

OTHER PUBLICATIONS

A. Fukuoka, Tanji Kinzoku Shokubai niyoru Cellulose Kara to Alcohol eno Henkan Hanno, Shokubai, vol. 48, No. 6, 2006, pp. 430-432.
Shackleton, et al. "Gas chromatographic and mass spectrometric analysis of urinary acidic metabolites of cortisol." Steroids, vol. 36, No. 3, Sep. 1980, pp. 289-298.
Erb et al. "Polymer-supported triazenes as smart reagents for the alkylation of carboxylic acids." Chemistry, vol. 9, No. 11, Jun. 6, 2003, pp. 2582-2588.
Zaia. "Mass spectrometry of oligosaccharides." Mass Spectrometry Reviews, vol. 23, No. 3, May 2004, pp. 161-227.
Lohse et al. "Solid-phase oligosaccharide Tagging (SPOT): validation on glycolypid-derived structures." Angewandte Chemie, vol. 118, Jun. 2006, pp. 4273-4278.
Miura et al. "Rapid and simple solid-phase esterification of sialic acid residues for quantitative glycomics by mass spectrometry." Chemistry, vol. 13, No. 17, 2007, pp. 4797-4804.
N. Dechamp et al., Kinetics of glucose hydrogenation in a trickle-bed reactor, Catalysis Today, vol. 24, 1995, pp. 29-34.
Burkhard Kusserow, Hydrogenation of Glucose to Sorbitol over Nickel and Ruthenium Catalysts, Advanced Synthesis and Catalysis, vol. 345, 2003, pp. 289-299.
Pierre Gallezot et al., Glucose Hydrogenation on Ruthenium Catalysts in a Trickle-Bed Reactor, Journal of Catalysts, vol. 180, 1998, pp. 51-55.
B. W. Hoffer et al., Carbon supported Ru catalysts as promising alternatives for Raney-type NI in the selective hydrogenation of D-glucose, Catalysis Today, vol. 79-80, 2003, pp. 35-41.
Atsushi Fukuoka, Catalytic Conversion of Cellulose into Sugar Alcohols, Angewandte Chemie International Edition, vol. 45, No. 31, Aug. 4, 2006, pp. 5161-5163.
Atsushi Fukuoka, Tanji Kinzoku Shokubal niyoru Cellulose Kara to Alcohol eno Henkan Hanno, Sokubal, vol. 48, No. 6, Sep. 10, 2006, pp. 430-432.

\* cited by examiner

CATALYST FOR CELLULOSE HYDROLYSIS AND/OR REDUCTION OF CELLULOSE HYDROLYSIS PRODUCTS AND METHOD OF PRODUCING SUGAR ALCOHOLS FROM CELLULOSE

This is a 371 of PCT/JP2007/ 053935 filed Mar. 1, 2007.

CROSS-REFERENCE TO RELATED PATENT APPLICATIONS

The present application claims priority under Japanese Patent Application 2006-54342, filed on Mar. 1, 2006, the entire contents of which are hereby incorporated by reference herein.

TECHNICAL FIELD

The present invention relates to a cellulose hydrolysis and reduction catalyst and to a method of producing sugar alcohols from cellulose. More particularly, the present invention relates to a catalyst permitting the direct production of sugar alcohols from cellulose and to a method of producing sugar alcohols from cellulose using this catalyst. The specific sugar alcohols that are produced by the present invention are sorbitol and/or mannitol.

BACKGROUND ART

The biomass is a renewable resource and plays a role in preventing global warming by inhibiting the emission of carbon dioxide. Processes of converting the biomass to ethanol, lactic acid, and other useful chemical products by an enzymatic or chemical method are being examined in the production of chemical products from the biomass (biorefinery). Currently, starch derived from corn is the main material employed in biorefinery. In terms of the quantity of resources of primary structural components of plants that are available, cellulose is present in overwhelmingly greater quantity than starch. However, the techniques to convert cellulose to chemically useful products by reducing the molecular weight thereof has not been developed, and this resource is currently virtually untapped. (See Koshijima et al., Functional Cellulose, CMC Publishing Co., Ltd. (2003), and The Japan Institute of Energy, ed., Biomass Handbook, Ohmsha (2002), the entire contents of which are hereby incorporated by reference herein.) For example, a large number of research has been conducted into degrading cellulose with enzymes. However, major problems remain with enzymatic methods because of low reaction rates and the need to greatly enhance activity and separate the enzyme from the product. Processes of obtaining glucose by hydrolysis with sulfuric acid or hydrofluoric acid have been attempted in the degradation of cellulose with catalysts. However, such processes have not been put into general practice due to corrosion of reactors with an acid, hazards, and the production of large amounts of neutralization waste becoming a major load on the environment.

In precedent researches of the chemical conversion of cellulose with catalysts, Balandin and Vasyunina, et al., have conducted hydrogenation with a supported ruthenium catalyst to produce sorbitol from sulfite cellulose with a yield of 82 percent (see A. A. Balandin, N. A. Vasyunina, G. S. Barysheva, S. V. Chepigo, Izv. Akad. Nauk SSSR, Ser. Khim., 392 (1957), the entire contents of which are hereby incorporated by reference herein.). However, there is no description of the use of cellulose itself as a raw material. Further, in this reaction, the use of sulfuric acid requires separation of the product, and presents problems in the form of the generation of neutralization waste and the corrosion of reactors. The same group employed silk cellulose that had been treated with alkali and acid as a raw material, and conducted hydrogenation with supported Raney nickel in the presence of nickel sulfate in an aqueous solution to obtain sorbitol (see N. A. Vasyunina, A. A. Balandin, G. S. Barysheva, S. V. Chepigo, Yu. L. Pogpsov, Z. Prik. Khim., 37, 2725 (1964), the entire contents of which are hereby incorporated by reference herein). Here again, the cellulose has to be pretreated and the product separation is not easy. Specht et al. used a mixture of cellulose and hemicellulose that had been treated by hydrolysis as a raw material, and after adjustment of its pH at 8 or greater, sugar alcohols was synthesized by hydrogenation with supported Raney nickel catalyst (see H. Specht and H. Dewein, DE 1066567 (1959), the entire contents of which are hereby incorporated by reference herein). However, cellulose pretreatment and pH adjustment were required.

Although cellulose is insoluble in water, most starches with similar structure are water soluble. Since hydrolysis and hydrogenation reactions of water-soluble starch proceed smoothly, a large number of research has been conducted in this area. Atlas Powder Corp. employed a Ni/diatomaceous earth catalyst to hydrogenate starch and obtain polyols (see Atlas Powder, GB 872809 (1961), the entire contents of which are hereby incorporated by reference herein).

Kruse et al. employed a Ru/USY catalyst to synthesize sorbitol from cornstarch in two-steps (see W. M. Kruse and L. W. Wright, U.S. Pat. No. 3,963,788 (1976), the entire contents of which are hereby incorporated by reference herein).

Jacobs et al. employed a Ru/USY catalyst to synthesize sorbitol in a single step (see P. Jacobs and H. Hinnekens, EP 0329923 (1989), Japanese Unexamined Patent Publication (KOKAI) Heisei No. 1-268653, or English family member EP 0329923A1; the entire contents of which are hereby incorporated by reference herein). Hydrogenation of water-insoluble cellulose is not conducted in the cited references. Moreover, the catalysts are limited to high-dispersion ones with a Ru dispersion of 0.58 or higher.

As shown above, in the conventional production of sugar alcohols, such as sorbitol, by the hydrolysis and hydrogenation of cellulose, the cellulose is always treated with an acid or an alkali to increase solubility in water, and then employed as a reaction substrate; there is no example of water-insoluble cellulose itself being used. Further, the need to separate the catalyst and product, adjust the pH, neutralize the acid or alkali, and activate the catalyst during reuse create problems in the form of a major load on the environment.

Accordingly, the objects of the present invention are to provide a catalyst for use in the production of sugar alcohols by the hydrolysis and hydrogenation of cellulose that permits the use of cellulose without pretreatment, that affords easy separation of catalyst and product, and that does not require pH adjustment, acid or alkali neutralization, or activation of the catalyst during reuse, and to provide a method for producing sugar alcohols from cellulose employing this catalyst.

DISCLOSURE OF INVENTION

To solve the above-stated problem, the present inventors conducted reactions with the aim of reducing the molecular weight of cellulose by using a solid catalyst. This resulted in the discovery that by conducting cellulose hydrolysis and hydrogenation reactions in water with pressurized hydrogen with a supported metal catalyst as indicated by the following reaction equation, sugar alcohols (sorbitol and mannitol) were synthesized in a single step.

[Chem. 1]

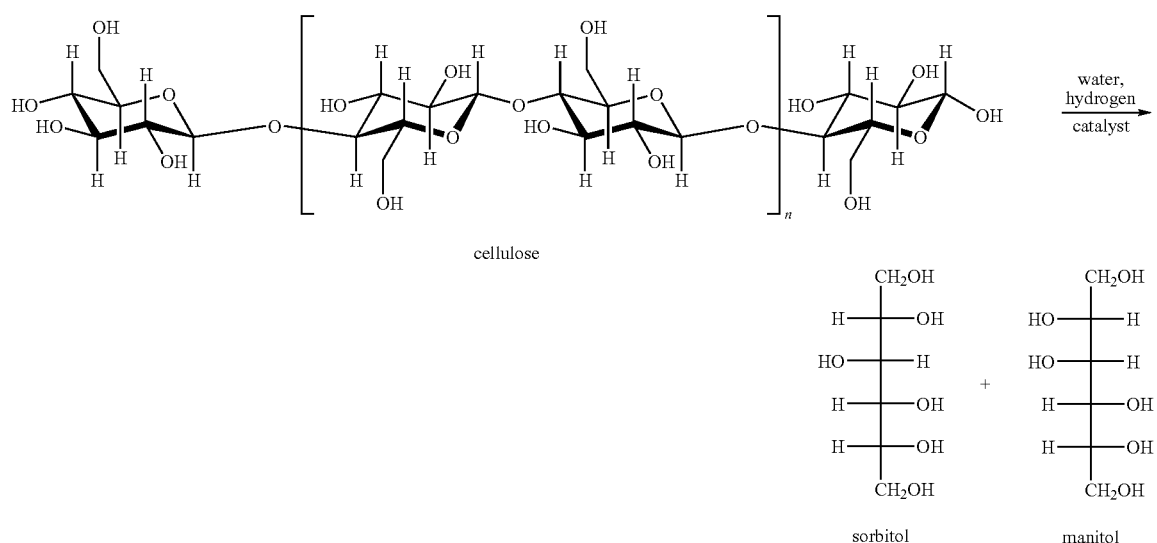

The present invention is as follows:

[1] A catalyst for cellulose hydrolysis and/or the reduction of hydrolysis products, in which a transition metal of group 8 to 11 is supported on a solid support.
[2] The catalyst according to [1], wherein at least a portion of said solid support is comprised of a porous material.
[3] The catalyst according to [1] or [2], wherein at least a portion of said solid support is comprised of an inorganic oxide.
[4] The catalyst according to any one of [1] to [3], wherein at least a portion of said solid support is comprised of a material exhibiting acidity.
[5] The catalyst according to any one of [1] to [4], wherein at least a portion of said solid support is at least one member selected from the group consisting of: silica, alumina, silica-alumina, zeolite, titania, zirconia, and activated carbon.
[6] The catalyst according to any one of [1] to [5], wherein said solid support is in powder form, particulate form, granular form, or pellet form; has a honeycomb structure or extruded shape; is in ring form or columnar form; has an extruded ribbed shape; or is in ribbed ring form.
[7] The catalyst according to any one of [1] to [5], wherein said transition metal is at least one member selected from the group consisting of: platinum, ruthenium, rhodium, palladium, iridium, nickel, cobalt, iron, copper, silver, and gold.
[8] The catalyst according to any one of [1] to [7], wherein said transition metal is supported on the surface of the solid support at a dispersion of 0.01 to 60.
[9] The catalyst according to any one of [1] to [8], wherein said transition metal is supported at 0.01 to 60 mass percent.
[10] The catalyst according to any one of [1] to [8], wherein the catalyst is employed for cellulose hydrolysis.
[11] The catalyst according to any one of [1] to [8], wherein the catalyst is employed for reduction of a cellulose hydrolysis product.
[12] The catalyst according to any one of [1] to [8], wherein the catalyst is employed for cellulose hydrolysis and for reduction of a cellulose hydrolysis product.
[13] A method of producing sugar alcohols comprising:
hydrolyzing cellulose in the presence of the catalyst described in any one of [1] to [9] in a hydrogen-containing atmosphere with pressurization; and
reducing the hydrolysis product of cellulose.
[14] The producing method according to [13], wherein said cellulose is alpha-cellulose having crystallinity or having reduced crystallinity.
[15] The producing method according to [13] or [14], wherein the hydrolysis and reduction are conducted in the presence of water.
[16] The producing method according to any one of [13] to [15], wherein said catalyst is employed in a mass ratio of 0.05 to 5 relative to cellulose.
[17] The producing method according to any one of [13] to [16], wherein the hydrogen-containing atmosphere has a hydrogen pressure of 1 to 100 MPa.
[18] The producing method according to any one of [13] to [17], wherein said hydrolysis and reduction are conducted with heating at 150 to 250° C.
[19] The producing method of any one of [13] to [18], wherein said sugar alcohols are sorbitol and/or mannitol.
[20] The producing method of any one of [13] to [19], wherein after completion of said hydrolysis and reduction, the reaction mixture is subjected to solid-liquid separation and separated into an aqueous solution comprising sugar alcohols and a solid comprising at least the catalyst and unreacted cellulose.

ADVANTAGES OF THE INVENTION

The present invention has the following features:
1. The fact that sugar alcohols (sorbitol and mannitol) can be directly synthesized employing cellulose as raw material has been discovered for the first time. The principal component of the sugar alcohols is sorbitol.
2. The fact that among catalysts, supported Pt and Ru catalysts exhibit high activity has been discovered. Catalysts corresponding to the previously patented Ru/HUSY (Ru/HUSY (2.9, $NH_3$, IE) in FIG. 1), which synthesize sorbitol from starch, exhibit only extremely low activity (a yield of 0.7 percent) in the present cellulose reaction. Accordingly, only with the recently discovered catalyst has the cellulose reaction become possible. Inorganic oxide supports exhibiting solid acidity afford high activity.

3. The catalyst that has been separated can be reused as is; activation processing is unnecessary.

Sorbitol is a sugar alcohol with three applications. The first application is that of sweetener, which is widespread in the food industry. The second is future application as an intermediate in the synthesis of useful compounds such as isosorbide, propylene glycol, ethylene glycol, glycerol, 1,4-sorbitan, and lactic acid. Isosorbide, in particular, is also employed in current processes, such as copolymerization during the production of polyethylene terephthalate (PET) to production polyethylene isosorbide terephthalate (PEIT). The PEIT polymer has a higher glass transition point than PET, so use in transparent plastic containers that can hold hot water is anticipated. The third application, also a future application, is as an intermediate in the production of hydrogen and liquid hydrocarbons (comprised mainly of C5 and C6 alkanes) that can be renewed from the biomass. Hydrogen is employed in fuel cells and hydrocarbons are a raw material for petrochemistry. Although hydrogen can be produced from glucose and sorbitol using supported metal catalysts, based on the research of Dumesic et al., the use of sorbitol as a raw materials affords greater hydrogen and alkane selectivity than glucose (J. A. Dumesic et al., *Chem. Commun.* 36 (2004)). Accordingly, application of the results of the present invention permits the production of hydrogen for fuel cells and hydrocarbons for the petrochemical industry employing cellulose as raw material with sorbitol as intermediate. Mannitol is an isomer (epimer) of sorbitol at the C2 position and has properties similar to those of sorbitol.

BEST MODE OF CARRYING OUT THE INVENTION

[The Catalyst]

The catalyst of the present invention, in which a transition metal of group 8 to 11 is supported on a solid support, catalyzes the hydrolysis of cellulose and/or the reduction of a hydrolysis product. The "hydrolysis product" referred to is a cellulose hydrolysis product, specifically glucose.

The Solid Support

At least a portion of the solid support employed in the catalyst of the present invention is suitably comprised of a porous material; it is also suitable for a transition metal to be supported on the surface of the porous material. Accordingly, the solid support employed in the catalyst of the present invention is suitably comprised of a porous material at least some portion of the surface of which supports a transition metal, and the solid support may be comprised of a porous material as a whole or may be comprised of a nonporous material the surface of which is coated with a porous material. The support may also be comprised of another porous material.

At least a portion of the solid support employed in the catalyst of the present invention can be comprised of an inorganic oxide, for example. The inorganic oxide is desirably the above-described porous material. Further, at least a portion of the solid support employed in the catalyst of the present invention is desirably in the form of a solid support exhibiting acidity, with the solid support exhibiting acidity desirably being the above-described porous material. Based on the results of research by the present inventors, the solid support desirably gives a proton acid site on the support, at which hydrogen molecules are dissociated by a metal such as Pt.

Specific example of the solid support are: silica, alumina, silica-alumina, zeolite, titania, zirconia, and activated carbon.

Among the silicas, examples of amorphous silicas are: Wako Pure Chemical Industries, Ltd.: Wakogels (C-100, C-100E, C-200, C-200E, C-300, C-300E, C-300HG, C-400HG, C-500HG, 50C18, 100C18, DX, FC-40, FC-40FM, G, LP-20, LP-40, LP-60, Q-12, Q-22, Q-23, Q-50, Q-63, and S-1); Wakosils (C-200, C-300, 25SIL, 25C18, 40SIL, and 40C18); Kanto Chemical Co., Inc.: silica gels (60 and 60N); Merck, Inc.: silica gels (40, 60, and 100); Sigma-Aldrich Japan K. K.: silica gels (03, 12, 15, 22, 40, 41, 62, 922, 923, high-purity grade, 70-230 mesh 60 A, 70-270 mesh 60 A, 130-270 mesh 60 A, and 200-400 mesh 60 A) and silicon dioxide (particle size 0.5-10 micrometers); Fuji Silysia Chemical, Ltd.: CARIACT (Q, G, and P); Grace Davison Co.: Davisil (633, 634, 635, 636, 643, 644, 645, 646, and 710); Degussa (Nippon Aerosil Co., Ltd.)): Aerosil (90, 130, 150, 200, 300, and 380); NIKKI CHEMICAL CO., LTD.: silica catalysts (N601, N601A, N601T, N601R3, N601A3, N601T3, N602, N602A, N602T, N608R, N608A, and N608T); Catalysis Society of Japan: silica reference catalysts (JRC-SIO-1, JRC-SIO-5, JRC-SIO-6, JRC-SIO-7, and JRC-SIO-9A); and Riedel-de Haën Co.: Cabosil M-5.

Examples of mesoporous silicas are those having pore diameters of 2 to 50 nm and surface areas of 500 to 1,500 m$^2$ g$^{-1}$, such as FSM-16 (S. Inagaki et al., *J. Chem. Soc., Chem. Commun.*, 680 (1993); MCM-41 (C. T. Kresge et al., Nature, 359, 710 (1992); J. S. Beck, et al. *J. Am. Chem. Soc.*, 114, 10834 (1992)); SBA-15 (D. Zhao, et al., *Science*, 279, 548 (1998); Taiyo Kagaku Co., Ltd.: NPM (nanoporous material, pore diameter 1-10 nm); and Sigma-Aldrich Japan K.K.: Silica (mesostructured, hexagonal framework, MCM-41 type).

Examples of alumina in the form of gamma-alumina are: Wako Pure Chemical Industries, Ltd.: activated alumina; Kanto Chemical Co., Inc.: aluminum oxide (alpha-type, NanoTek, activated); Merck Inc.: Alumina (90, 90 (activated, acidic, activity I), 90 (activated, basic, activity I), and 90 (activated, neutral, activity I)); Sigma-Aldrich Japan K.K.: aluminum oxide (99.99 percent, −100 mesh 99.9 percent, powder <10 micrometers, nanopowder, nanopowder whiskers, −100 mesh 99 percent, pellets 3 mm, activated acidic Brockmann I, activated weakly acidic Brockmann I, activated basic Brockmann I, activated neutral Brockmann I, fused); Nishio K.K.: gamma-alumina A-11; NIKKI CHEMICAL CO., LTD.: alumina catalysts (N611N, N611N3, N612N, and N613N); and the Catalysis Society of Japan: alumina reference catalysts (JRC-ALO-1, JRC-ALO-2, JRC-ALO-3, JRC-ALO-5, JRC-ALO-1A, JRC-ALO-5A, JRC-ALO-6, JRC-ALO-7, and JRC-ALO-8).

Examples of titania comprise the rutile, anatase, and amorphous forms, specifically: Wako Pure Chemical Industries, Ltd.: titanium (IV) oxide (amorphous, anatase, and rutile forms, 80 nm); Kanto Chemical Co., Inc.: titanium (IV) oxide (rutile and anatase forms, 3N, NanoTek); Sigma-Aldrich Japan K.K.: Titanium(IV) oxide (99.999 percent, 99.99 percent, mesoporous 32 Angstrom pore 99.95 percent, powder <5 microns 99.9+ percent, powder 99.9+ percent, −325 mesh 99+ percent; Japan Aerosil Co., Ltd.: Aeroxide TiO$_2$ (NKT90, P25, PF2, and T805); Sakai Chemical Industry Co., Ltd.: titanium oxides (SR-1, R-42, R-GL, R-GX, R-GX-2, R-45M, R-650, R-32, R-5N, R-5N-2, R-61N, R-62N, R-7E, R-3L, R-3L-SN, R-11P, R-21, R-25, R-310, D-918, A-110, A-150, ST-G, A-190, SA-1, and SA-1 L); Ishihara Sangyo Kaisha, Ltd.: ultrafine particulate titanium oxide (TTO-51 (A), TTO-51 (C), TTO-55(A), TTO-55(B), TTO-55(C), TTO-55(D), TTO-S-1, TTO-S-2, TTO-S-3, MPT-136, TTO-V-3, TTO-V-4, TTO-F-2, and TTO-F-6), neutral titaniasol TSK-5, catalyst supporting titanium oxides (MC-50, MC-90, MC-150), and photocatalytic titanium oxides (ST-01, ST-21, ST-31, ST-41, and ST-30L); and the Catalysis Society of Japan: titania reference catalysts (JRC-TIO-1, JRC-TIO-2, JRC-TIO-4, JRC-TIO-5, JRC-TIO-6, JRC-TIO-7, JRC-TIO-8, JRC-TIO-9, JRC-TIO-10, JRC-TIO-11, JRC-TIO-12, and JRC-TIO-13).

Examples of silica-alumina are Sigma-Aldrich Japan K.K.: silica-alumina catalyst support grade 135; NIKKI CHEMICAL CO., LTD.: silica-alumina (N631 L, N631HN, N632L, N632HN, N633L, and N633HN), and the Catalysis Society of Japan: silica-alumina reference catalysts (JRC-SAH-1 and JRC-SAL-2).

Examples of zeolite are:
beta-type (structural code BEA, hereinafter same): Catalysis Society of Japan: zeolite (beta) reference catalysts JRC-Z-B25(1), JRC-Z-HB25(1), JRC-HB150(1); Zeolyst Co.: CP814N*, CP814E*, CP814C*, CP814Q*, CP811E-150, CP811C-300; Tosoh Corporation: 930NHA, 940NHA, and 940HOA;
Y-type (FAU): Sigma-Aldrich Japan K.K.: molecular sieve catalyst support, sodium Y zeolite, powder; molecular sieves catalyst support, ammonium Y zeolite, powder; Catalysis Society of Japan: zeolite (Y-type) reference catalysts JRC-Z-Y4.8, JRC-Z-Y5.6, JRC-Z-HY4.8(2), JRC-Z-Y5.5, JRC-Z-Y5.3, JRC-Z-HY5.5, and JRC-Z-HY5.3; UOP LLC: Y-52 (NaY), Y-64($NH_4$Y), Y-74(HY), Y-84($NH_4$Y), and LZ-15 (HY); Zeolyst Co.: CBV100, CBV300, CBV400, CBV 600, CBV 712, CBV 720, CBV 740, CBV760, CBV780, and CBV 901); Tosoh Corporation: 320NAA, 320HOA, 331HSA, 341NHA, 350HUA, 360HUA, 385HUA, and 390HUA; and Catalysts & Chemicals Ind. Co., Ltd.: ZCP-50S, ZCP-50, ZCP-150, ZCP-300, ZCP-700, ZCP-1000, ZCP-2000, ZCE-50S, ZCE-50, ZCE-150 to 2000, ZCB-50S, and ZCB-2000. In the present application, when referring to Y-type zeolites, the dealuminated Y-type zeolites is referred to as "USY" and those that have not been so processed simply as "Y". Accordingly, those in which the cation is a proton is referred to as "HUSY" and "HY," respectively.
ZSM-5 type (MFI): Catalysis Society of Japan: zeolite (ZSM-5) reference catalysts: JRC-Z5-25H, JRC-Z5-70H, JRC-Z5-1000H, JRC-Z5-70NA, JRC-Z5-1000NA, JRC-Z5-90NA (1), and JRC-Z5-90H(1); and Zeolyst Co.: CBV2314, CBV3020E, CBV3024E, CBV5524G, CBV8014, and CBV28014.
Mordenite zeolite (MOR): Catalysis Society of Japan: zeolite (mordenite) reference catalysts JRC-Z-M15(1), JRC-Z-M20 (1), JRC-Z-HM20(5), JRC-Z-HM90(1); Zeolyst Co.: CBV10A, CBV21A, and CBV90A; and Tosoh Corporation: 642NAA, 640HOA, and 690HOA. Among those cited above, USY type with dealumination treatment is desirable.

Examples of activated carbon are: Wako Pure Chemical Industries, Ltd.: activated carbon (for chromatography, comminuted form 0.2 to 1 mm, comminuted form 2 to 5 mm, granular form, powder form, powder acid-washed, powder alkaline, powder neutral, rod-shaped); Kanto Chemical Co., Inc.: activated carbon (particulate and powder); Sigma-Aldrich Japan K.K.: activated carbon granules 4 to 14 mesh; Norit Japan Co., Ltd.: PK, PKDA 10×30 MESH (MRK), ELORIT, AZO, DARCO, HYDRODARCO 3000/4000, DARCO Li, PETRODARCO, DARCO MRX, GAC, GAC PLUS, DARCO VAPURE, GCN, C GRAN, ROW/ROY, RO, ROX, RB/W, R, R.EXTRA, SORBONORIT, GF 40/45, CNR, ROZ, RBM, RBHG, RZN, RGM, SX, SA, D 10, VETERINAIR, PN, ZN, SA-SW, W, GL, SAM, HB PLUS, A/B/C EUR/USP, CA, CN, CG, GB, CAP/CGP SUPER, S-51, S-51 A, S-51 HF, S-51 FF, DARCO GFP, HDB/HDC/HDR/HDW, GRO SAFE, DARCO INSUL, FM-1, DARCO TRS, DARCO FGD/FGUHg/Hg-LH, and PAC 20/200; Japan EnviroChemicals, Ltd.: Shirasagi (A, C, DO-2, DO-5, DO-11, FAC-10, M, P, PHC, Element DC), Aldenite, Carboraffin, Carboraffin DC, honeycomb carbo Shirasagi, Morshibon, strong Shirasagi, purified Shirasagi, special order Shirasagi, X-7000/X7100, X7000-3/X-7100-3, LPM006, LPM007, and particulate Shirasagi (APRC, C2c, C2x, DC, G2c, G2x, GAAx, GH2x, GHxUG, GM2x, GOC, GOHX, GOX, GS1x, GS2x, GS3x, GTx, GTsx, KL, LGK-100, LGK-400, LGK-700, LH2c, MAC, MAC-W, NCC, S2x, SRCX, TAC, WH2c/W2c, WH2x, WH5c/W5c, WHA, X2M (Morshibon 5A), XRC, X7000H/X7100H, X7000H-3/X7100-3, LGK-700, and DX7-3); Kuraray Chemical Co., Ltd: gas phase-use particulate activated carbons GG/GS/GA; gas phase-use activated carbons GW/GL/GLC/KW/GWC; and powder activated carbons PW/PK/PDX; Calgon Mitsubishi Chemical Carbon: Diahope (006, 006S, 007, 008, 008B, 008S, 106, 6D, 6MD, 6MW, 6W, S60, C, DX, MM, MZ, PX, S60S, S61, S70, S80, S80A, S80J, S80S, S81, ZGA4, ZGB4, ZGN4, ZGR3, ZGR4, ZS, ZX4, and ZX-7), Diasorp (F, G4-8, W 8-32, W 10-30, XCA-C, XCA-AS, and ZGR4-C), and Calgon (AG 40, AGR, APA, AP3-60, AP4-60, APC, ASC, BPL, BPL 4×10, CAL, CENTAUR 4×6, CENTAUR 8×30, CENTAUR 12×40, CENTAUR HSV, CPG 8×30, CPG 12×40, F-AG 5, Filtrasorb 300, Filtrasorb 400, GRC 20, GRC 20 12×40, GRC 22, HGR, HGR-LH, HGR-P, IVP 4×6, OL 20×50, OLC 20×50, PCB, PCB 4×10, RVG, SGL, STL 820, URC, WS 460, WS 465, WS 480, WS490, and WSC 470); Ajinomoto Fine-Techno Co., Inc.: BA, BA-H, CL-H, CL-K, F-17, GS-A, GS-B, HF, HG, HG-S, HN, HP, SD, Y-180C, Y-4, Y-4S, Y-10S, Y-10SF, YF-4, YN-4, YP, and ZN; and Cataler Corporation: A series, BC-9, BFG series, CT series, DSW series, FM-150, FW, FY series, GA, PG series, and WA series. Activated carbon with a surface area of 800 to 1,500 $m^2\ g^{-1}$ is desirable.

Neither the shape nor the form of the solid support is specifically limited. However, for example, powder form, particulate form, granular form, pellet form, or honeycomb form; an extruded shape; a ring form or columnar form; an extruded ribbed shape; or a ribbed ring form can be used. A support that is in the form of a powder, particle, grain, or pellet, for example, can be comprised solely of the above-described porous material, oxide, or material exhibiting acidity. By contrast, a support of honeycomb structure can be comprised of a nonporous material, such as a support comprised of cordierite or the surface of which is coated with a porous material, oxide, or material exhibiting acidity. This support can also be comprised of another porous material.

The transition metal is at least one member selected from the group consisting of platinum, ruthenium, rhodium, palladium, iridium, nickel, cobalt, iron, copper, silver, and gold. These transition metals may be employed singly or in combinations of two or more. From the perspective of high catalytic activity, the transition metal is desirably selected from among the platinum group of metals consisting of platinum, ruthenium, rhodium, palladium, and iridium.

The transition metal is suitably supported on the surface of the solid support with a dispersion of 0.01 to 0.95, desirably 0.1 to 0.9, and preferably, 0.3 to 0.8. The lower the dispersion, the lower the rate of proton formation from the hydrogen molecules due to metal aggregation, thus decreasing the reaction rate. The dispersion of the transition metal can be adjusted by the amount of transition metal compound employed as the starting material, the temperature conditions (rate of temperature rise and maximum temperature) of oxygen calcination during catalyst preparation, and the temperature conditions during hydrogen reduction (rate of temperature rise and maximum temperature).

The amount of transition metal that is supported on the solid support can be suitably determined in consideration of the type and the dispersion of the transition metal, and is, for example, suitably 0.01 to 50 mass percent, desirably 0.01 to 30 mass percent, and more preferably, 0.01 to 10 mass percent, of the catalyst.

The catalyst of the present invention can be produced by referencing conventional methods for preparing metal-supporting solid catalysts. For example, preparation is possible in the following manner by the impregnation method.

The support is vacuum dried for one hour at 150° C. Next, water is added to prepare a dispersion liquid. To this is added an aqueous solution containing a prescribed quantity of a metal salt and the mixture is stirred for 15 hours. Subsequently, the water is evaporated off under reduced pressure to obtain a solid, which is calcined for 2 hours at 400° C. under an oxygen gas flow. The product is then reduced for 2 hours at 400° C. under a hydrogen gas flow to obtain a catalyst in solid form (see the flowchart below).

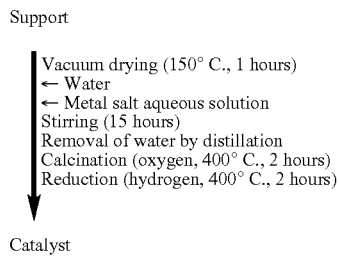

The catalyst of the present invention is employed to reduce a hydrolysis product of cellulose. That is, it can be used to prepare sugar alcohols by reducing glucose, which is a hydrolysis product of cellulose. Alternatively, the catalyst of the present invention is employed to hydrolyze cellulose and reduce the hydrolysis product of the cellulose. That is, it can be used to prepare sugar alcohols by hydrolyzing cellulose to obtain glucose and then reducing the glucose. The cellulose that is hydrolyzed by the catalyst of the present invention will be described in detail in the method for producing sugar alcohols below.

[The Method of Producing Sugar Alcohols]

The method of producing sugar alcohols of the present invention comprises the steps of hydrolyzing cellulose in a hydrogen-containing atmosphere in the presence of the above-described catalyst of the present invention and reducing the hydrolysis product of cellulose.

The cellulose serving as the raw material is not specifically limited; commercially available cellulose in powder form can be employed as is. The cellulose is of plant form, and may be, for example, water-insoluble alpha-cellulose obtained by bleaching a defatted wood powder with a chlorine treatment to obtain a chemical pulp (holocellulose), which is then subjected to an alkali treatment to remove the hemicellulose.

Generally, in cellulose, two or more alpha-cellulose units are bonded together by hydrogen bonds and exhibit crystallinity. In the present invention, cellulose exhibiting such crystallinity can be employed as the starting material, or such crystalline cellulose can be treated to reduce the crystallinity and the resulting cellulose of reduced crystallinity can be employed. The cellulose of reduced crystallinity can be cellulose the crystallinity of which has been partially reduced, or cellulose in which the crystallinity has been completely, or nearly completely, eliminated. The type of processing used to reduce crystallinity is not specifically limited, but a crystallinity-reducing process capable of cleaving the above hydrogen bonds and at least partially producing single-chain alpha-cellulose is desirable. The use of a starting material in the form of cellulose at least partially comprising single-chain alpha-cellulose greatly enhances the efficiency of hydrolysis.

The process used to reduce the crystallinity of the starting material cellulose can be a method of obtaining single-chain alpha-cellulose by physically cleaving the hydrogen bond of alpha-cellulose such as a ball mill processing (see H. Zhao, J. H. Kwak, J. A. Franz, J. M. White, J. E. Holladay, *Energy & Fuels*, 20, 807 (2006), the entire contents of which are hereby incorporated by reference herein), or a method of obtaining single-chain alpha-cellulose by chemically cleaving the hydrogen bond of alpha-cellulose such as a phosphoric acid processing (see Y.-H. P. Zhang, J. Cui, L. R. Lynd, L. Kuang, *Biomacromolecules*, 7, 644 (2006), the entire contents of which are hereby incorporated by reference herein), for example. Even when the processing to reduce the crystallinity of cellulose does not completely eliminate the crystallinity of the cellulose, as described in Embodiment 7, the efficiency of hydrolysis is greatly enhanced by employing cellulose as the starting material, the crystallinity of which has been partially reduced comparing to that prior to such processing.

A further example of a process for reducing the crystallinity of cellulose is processing with pressurized hot water (see N. Hayashi, S. Fujita, T. Irie, T. Sakamoto, M. Shibata, *J. Jpn. Inst. Energy*, 83, 805 (2004), and M. Sasaki, Z. Fang, Y. Fukushima, T. Adschiri, K. Arai, *Ind. Eng. Chem. Res.*, 39, 2883 (2000), the entire contents of which are hereby incorporated by reference herein).

The hydrolysis and reduction are conducted in the presence of water. The quantity of water present is at least enough to hydrolyze the entire quantity of cellulose, and desirably falls within a mass range of 5 to 500, for example, relative to the cellulose when the fluidity and stirring properties of the reaction mixture are taken into account.

The quantity of catalyst employed can be suitably determined in consideration of the activity of the catalyst and the reaction conditions (such as the temperature, duration, and hydrogen pressure). For example, a mass ratio falling within a range of 0.05 to 5 relative to the cellulose is suitable.

The reaction atmosphere is a hydrogen-containing atmosphere. The hydrogen-containing atmosphere, for example, suitably consists of a hydrogen pressure of 1 to 100 MPa, desirably 1.5 to 50, and more preferably, 2 to 20 MPa.

The hydrolysis and reduction are, for example, suitably conducted at 150 to 250° C. with heating, desirably 180 to 250° C. with heating, and more preferably, 190 to 210° C. with heating.

The reaction time of the hydrolysis and reduction can be suitably determined by taking into account the scale of the reaction, the reaction conditions, the amounts of catalyst and cellulose employed, and the like. Normally, a reaction time of 1 to 100 hours is suitable. The reaction can be conducted in batch-type, continuous flow-type, or the like. The reaction is desirably conducted by stirring the reaction mixture.

Once the hydrolysis and reduction have ended, the reaction mixture can be subjected to solid-liquid separation, the aqueous solution containing the sugar alcohols can be recovered as a liquid phase, and solids including at least the catalyst and unreacted cellulose can be separated out as the solid phase. The method of solid-liquid separation is not specifically limited, and may be suitably determined based on the usual methods in consideration of the shape and form of the catalyst, the amount of unreacted cellulose present, and the like. For example, methods such as filtration, centrifugation, and precipitation can be employed. The solid containing the catalyst and unreacted cellulose can be employed in the next reaction.

The catalyst of the present invention does not specifically require activation for reuse. However, for example, the usual activation of metal-supported solid catalysts can be employed prior to reuse.

In the catalyst activation process, the catalyst can be washed with water and dried and the metal and residual organic compounds on the support can be removed by thermal degradation with heating for 1 to 5 hours at 200 to 500° C. under a hydrogen gas flow while returning the surface of the supported metal to a reduced state for use.

[Embodiments]

The present invention will be described in detail below through embodiments.

[Embodiment 1]

1.1 Preparation of Catalysts

Catalyst supports in the form of amorphous silica (denoted as $SiO_2$ hereinafter: CARIACT Q-10 made by Fuji Silysia Chemical, Ltd.), mesoporous silica (FSM-16, prepared in-house (S. Inagaki, et al., *J. Chem. Soc., Chem. Commun.*, 680 (1993))), gamma-alumina (gamma-$Al_2O_3$, made by Nishio K. K. A-11), titania ($TiO_2$, Merck, Inc.), zirconia ($ZrO_2$, Wako Pure Chemical Industries, Ltd.), silica-alumina ($SiO_2$—$Al_2O_3$, Sigma-Aldrich Japan K.K. grade 135), HY (Zeolyst Co., CBV600, Si/Al atomic ratio of 2.6), HUSY (Zeolyst Co., CBV720 (Si/Al ratio 15), 740 (Si/Al ratio 20), 760 (Si/Al ratio 30), 780 (Si/Al ratio 40)), HUSY (Catalysts & Chemicals Ind. Co., Ltd. ZCP-2000, Si/Al ratio 100), ZSM-5 (Zeolyst Co. CBV4024E), H-beta (Catalysis Society of Japan, catalyst JRC-Z-B25(1)), HMOR (Catalysis Society reference catalyst JRC-Z-M15(1)), activated carbon (Takeda Pharmaceutical Co., Ltd. (now, Japan EnviroChemicals, Ltd.), LPM007) were employed. HUSY prepared from NaY (Union Carbide LZY-52) by the method described in Patent References 4 and 5 was found to have a Si/Al ratio of 2.9 by fluorescence X-ray analysis. Hereinafter, to distinguish HUSY, the Si/Al atomic ratio will be shown in parentheses and a notation such as HUSY (40) will be employed. ZSM-5 was calcined in air at 550° C. for 8 hours to obtain HZSM-5. The support was pretreated by heating under vacuum at 150° C. for 1 hour and then used for catalyst preparation. Metal precursors were commercially available chloroplatinic acid ($H_2PtCl_6 \cdot xH_2O$), ruthenium chloride ($RuCl_3 \cdot xH_2O$), hexaammineruthenium chloride ($[Ru(NH_3)_6]Cl_3$), rhodium chloride ($RhCl_3 \cdot xH_2O$), palladium chloride ($PdCl_2$), iridium chloride ($IrCl_3 \cdot xH_2O$), and nickel chloride ($NiCl_2 \cdot 6H_2O$). Since $PdCl_2$ was insoluble in water, a small amount of hydrochloric acid was added and vacuum distillation was conducted in an evaporator to obtain water-soluble $H_2PdCl_4$. The other metal salts were employed as is. Ion-exchange water was employed as the water.

The example of Pt/HUSY (40) will be described below as the method of preparing a catalyst. HUSY (40) powder (200 mg) was heated at 150° C. for 1 hour using a vacuum line and dried (degree of vacuum about $10^{-3}$ Torr=0.13 Pa). The mixture was cooled to room temperature and water (20 mL) was added to disperse the powder. To this was added an aqueous solution (5 mL) of $H_2PtCl_6 \cdot xH_2O$ (15 mg) and the mixture was stirred for 15 hours at room temperature. Subsequently, the water was evaporated off in an evaporator. The powder obtained was vacuum dried at room temperature for 2 hours in a vacuum line. Next, the powder was charged in a U-shaped glass tube and calcined by heating at 400° C. for 2 hours under an oxygen gas flow (flow rate 20 mL/minute). After cooling to room temperature, nitrogen gas was passed through to remove the oxygen, and under a hydrogen gas flow (flow rate 20 mL/minute), the mixture was reduced by heating for 2 hours at 400° C. After cooling to room temperature, nitrogen gas was passed through to remove the hydrogen, and the powder was recovered. The amount of metal supported in the catalyst was 60 mass percent for Ni/$SiO_2$—$Al_2O_3$, but 2.5 mass percent for other catalysts. For catalysts in which Ru was supported on HUSY (2.9), $[Ru(NH_3)_6]Cl_3$ was employed as starting material and the ion-exchange (IE) method (Patent References 4 and 5) was employed to prepare Ru/HUSY (2.9, $NH_3$, IE). The impregnation-evaporation to dryness (IMP) method was employed using $[Ru(NH_3)_6]Cl_3$ to prepare Ru/HUSY (2.9, $NH_3$, IMP), and the impregnation-evaporation to dryness method was employed on $RuCl_3 \cdot xH_2O$ to prepare Ru/HUSY (2.9, Cl, IMP). The catalytic activity of these compounds was compared. In addition, HUSY (20) support was impregnated with $RuCl_3 \cdot xH_2O$ and the evaporation to dryness method was employed to prepare Ru/HUSY (20, Cl, IMP) as a catalyst for use.

The dispersion by carbon monoxide adsorption by the pulse method (CO/Pt, measured with a Chembet-3000 made by Quantachrome Instruments) is shown in Table 1. The dispersion of Pt varied significantly based on the support. The dispersion of the Ru catalyst, at about 0.01 to 0.03, was lower than that described in Patent References 4 and 5. This was attributed to the Ru surface being sensitive to air and the surface being oxidized by trace amounts of air that mixed in during the operation. However, when this Ru catalyst was employed to hydrolyze and hydrogenate starch, it exhibited the same high activity described in Patent References 4 and 5 and did not exhibit diminished catalytic performance. Thus, it was employed unaltered in subsequent tests.

[Table 1]

TABLE 1

Dispersion of various catalysts by CO adsorption

| Catalyst | Dispersion (CO/Pt) |
|---|---|
| Pt/FSM-16 | 0.44 |
| Pt/$SiO_2$ | 0.08 |
| Pt/gamma-$Al_2O_3$ | 0.50 |
| Pt/HUSY(20) | 0.41 |
| Pt/C | 0.03 |
| Pt/$ZrO_2$ | 0.08 |
| Pt/$TiO_2$ | 0.18 |
| Ru/FSM-16 | 0.005 |
| Ru/$SiO_2$ | 0.02 |
| Ru/HUSY(20, Cl, IMP) | 0.01 |
| Ru/HUSY(2.9, $NH_3$, IE) | 0.026 |
| Pd/FSM-16 | 0.08 |
| Ir/FSM-16 | 0.16 |
| Rh/FSM-16 | 0.39 |

1.2 Catalytic Reaction

The reaction procedure for Pt/HUSY (40) is shown. These conditions will be referred to as the "standard conditions" hereinafter. To a stainless-steel autoclave (Taiatsu Techno Corp., model TPR2, 30 mL capacity) were charged 0.16 g of cellulose (Merck, Inc., microcrystals, 80 percent or more having a particle diameter of 20 to 160 micrometers), Pt/HUSY (40) (0.068 g), 20 g of water, and a stirrer, and the autoclave was closed. Here, the number of mols S of $C_6H_{10}O_5$ units in the cellulose was 0.99 mmols and the total number C of atoms of metal in the catalyst was adjusted to be S/C=110.

When changing the catalyst, the mass of the catalyst was adjusted to achieve S/C=110; 0.068 g of Pt catalyst, 0.036 g of Ru catalyst, 0.037 g of Rh catalyst, 0.037 g of Pd catalyst, 0.068 g of Ir catalyst, and 0.009 g of Ni catalyst were employed. Next, 5 MPa of hydrogen gas was introduced at room temperature. The autoclave was placed in a 190° C. oil bath and the reaction was conducted for 24 hours while stirring with a magnetic stirrer. Subsequently, the autoclave was cooled to room temperature, the remaining hydrogen gas was removed, the autoclave was returned to ambient pressure, the autoclave was opened, and the contents were recovered.

The product was analyzed with a liquid chromatograph (Shimadzu Corp. LC10ATVP, differential refractive index detector, column: Shodex Asahipak NH2P-50 4E or Shimadzu Shim-pack SPR-Ca). The sugar alcohols (sorbitol and manitol) were identified by liquid chromatography mass spectrometry (Shimadzu LCMS-2010A). The sorbitol yield was the ratio of the number of mols P of sorbitol produced to the number of mols S of $C_6H_{10}O_5$ units of cellulose charged: the sorbitol yield (percentage)=(number of mols P of sorbitol produced)/(number of mols S of $C_6H_{10}O_5$ units of cellulose charged)×100. The mannitol yield was similarly calculated.

[Embodiment 2]

The results of the reaction conducted under the standard conditions using the various supported metal catalysts are given in FIG. 1. In almost all cases, cellulose hydrolysis and hydrogenation proceeded catalytically and sugar alcohols were produced, with sorbitol being the primary product. For example, the yield of sugar alcohols produced with the Pt/gamma-$Al_2O_3$ catalyst was 18 percent, of which sorbitol comprised 15 percent and mannitol 3 percent. Similar product selectivity was achieved with the other catalysts. Under these reaction conditions, Pt/HUSY (40) and Pt/$SiO_2$—$Al_2O_3$ produced sugar alcohol yields of 20 percent or higher and afforded high activity. The activity order of the metals was: Pt>Ru>Pd>Rh>Ni>Ir. For Pt, the order of activity based on supports is given in FIG. 2. The sequence was: HUSY (40), $SiO_2$—$Al_2O_3$>HUSY (20), gamma-$Al_2O_3$>HZSM-5, HUSY (30)>HUSY (15)>HUSY (100), H-beta>FSM-16, $SiO_2$, HY (2.6), $TiO_2$>$ZrO_2$>C (activated carbon), HUSY (2.9), HMOR. Activity was highest for HUSY (40) and $SiO_2$—$Al_2O_3$, while the yields were low for $ZrO_2$, activated carbon, HUSY (2.9), and HMOR. Based on these results, it was surmised that those inorganic oxides exhibiting acidity were effective as supports, but the acidity did not directly correspond to the order of acid strength of the supports. Accordingly, the main active site of cellulose hydrolysis was not the acid sites inherently present on the support. Instead, it is suggested the hydrogen molecules were dissociated by Pt and Ru under hydrogen pressure conditions, moving onto the support (the spillover phenomenon) and creating proton acid sites (Hattori, *Shokubai*, 45, 327 (2003)). Actually, as shown in FIG. 3, when the reaction was conducted under similar conditions employing the various supports without the metals, only a small amount of glucose was produced. This results indicates that supporting the metals promotes hydrolysis.

The supported Ru catalyst exhibited activity in catalyzing and hydrogenating cellulose. However, interestingly, a catalyst (Patent References 4 and 5) employing HUSY (2.9) that was prepared from LZY-52, which was reported in prior art as having exhibited high activity in starch hydrolysis and hydrogenation, afforded an extremely low yield of 3 percent or lower regardless of the catalyst preparation and a Ru precursor. However, the Ru catalyst employing HUSY (20) as support afforded a sugar alcohol yield of 17 percent.

[Embodiment 3]

The dependence on reaction temperature of the sugar alcohol yield by Pt/gamma-$Al_2O_3$ catalyst was examined. Except for the reaction temperature, the standard conditions were employed. As shown in FIG. 4, the sugar alcohol yield at 180° C. was 14 percent, increased to 18 percent at 190° C. However, at 200° C., the yield decreased to 16 percent. Thus, 190° C. was the optimal temperature.

[Embodiment 4]

The sugar alcohol yields for reaction times of 24 and 72 hours are shown in FIG. 5. Except for the reaction time, the standard conditions were employed. For the three catalysts, the sugar alcohol yield increased little at 72 hours. For each catalyst, the peaks of unidentified by-products were found to increase on the liquid chromatograph at a reaction time of 72 hours.

[Embodiment 5]

Reuse of the catalysts was examined. The first reaction was conducted under the standard conditions using Pt/gamma-$Al_2O_3$ as catalyst. Following the reaction, the reaction mixture was placed on a centrifugal separator, the solid was sedimented, and the solid was separated by filtering the supernatant solution. As shown in FIG. 6, the sugar alcohol yield at the time was 18 percent. The separated solid was replenished with cellulose, water was added, and the reaction was similarly conducted. The sugar alcohol yield was 15 percent in the second reaction and 15 percent in the third reaction. These values were almost the same as that in the first reaction. Accordingly, it was found that the catalyst could be reused without activation treatment.

[Embodiment 6]

A test was conducted in which the charge stock was tripled. That is, to an autoclave were charged 0.4807 g of cellulose, 0.209 g of Pt/gamma-$Al_2O_3$, and 60 g of water. Hydrogen was introduced at an initial pressure of 5 MPa and the mixture was reacted for 24 hours at 190° C. Following the reaction, the solid (catalyst and cellulose) was separated from the aqueous phase by centrifugation. Analysis of the aqueous phase by liquid chromatography revealed a sugar alcohol yield of 28 percent, which converted to a mass of 0.135 g. When the aqueous phase was evaporated to dryness, 0.223 g of an oily substance was obtained. Accordingly, the sugar alcohol selectivity (based on mass) in the aqueous solution was 61 percent. The remaining by-products were unidentified.

[Embodiment 7]

Pretreatment of Cellulose (1)

Phosphoric acid treatment was conducted based on the method of Y.-H. P. Zhang, J. Cui, L. R. Lynd, L. Kuang, *Biomacromolecules*, 7, 644 (2006). To a polypropylene bottle (with a capacity of 250 mL) were charged 1.0 g of cellulose (Merck, Inc., Avicel, micropowder) and 30 mL of distilled water, a magnetic stirrer was introduced, and the mixture was stirred for 5 minutes at room temperature. Next, 55 mL of ice-cooled phosphoric acid (Kanto Chemical Co., Ltd., special grade) was added and the mixture was vigorously stirred while being cooled with ice to about 4° C. The stirring operation was conducted by vigorous stirring for 10 minutes and then halting stirring and allowing the mixture to stand for 2 to 3 minutes. This process was repeated for a total of one hour. In this operation, 5 minutes after the phosphoric acid was added all the cellulose was dissolved, giving a uniform aqueous solution. Subsequently, when 200 mL of ice-cooled water was added, the cellulose precipitated as a white powder, which was separated by centrifugal separation. The white powder obtained was washed 5 times with water; the aqueous solution had a pH of 2.5 to 3.0. Next, 2 mL of 2M calcium carbonate aqueous solution was added and the washing was repeated in a neutralization process that resulted in a pH of close to 6.0 to 7.0. Subsequently, the white powder was washed 5 to 6 times with water. The white powder obtained was dried at 60° C. under reduced pressure in a rotary evaporator and then placed in a desiccator containing silica gel and dried overnight. After drying, 0.96 g of white powder was obtained.

Pretreatment of Cellulose (2)

Ball milling treatment was conducted based on the method of H. Zhao, J. H. Kwak, J. A. Franz, J. M. White, J. E. Holladay, *Energy & Fuels*, 20, 807 (2006). To a ceramic pot mill with a capacity of 900 mL were charged 1 kg of zirconia beads (10 mm in diameter) and 10 g of cellulose (Merck Inc., Avicel, micropowder). Grinding was conducted for 2 hours at 60 rpm with a bench pot mill rotating base (AS ONE Corp., ANZ-51S). No medium such as water was employed. After the treatment, 0.9 g of powder was recovered and employed in the catalytic reaction as it was.

FIG. 7 shows the results of X-ray powder diffraction of unreacted, phosphoric acid-treated, and ball mill-treated cellulose. In the unreacted cellulose, a strong diffraction peak derived from the (002) crystal plane of cellulose I was observed in the vicinity of 2theta=23 degrees. However, after the treatment with phosphoric acid or the ball milling, the peak intensity greatly diminished, indicating that the crystalline structure collapsed.

The Catalytic Reaction

A 100 mL stainless-steel autoclave (OM Labotech Corp., MMJ-100) was used as a reactor and a test was conducted at triple the reaction scale of Embodiment 1. The catalysts employed were: gamma-alumina-supported Pt catalyst (Pt/Al$_2$O$_3$, 0.21 g), HUSY zeolite (Si/Al ratio of 20)-supported Pt catalyst (Pt/HUSY (20), 0.21 g), and gamma-alumina-supported Ru catalyst (Ru/Al$_2$O$_3$, 0.11 g). These catalysts were prepared by the impregnation method using chloroplatinic acid or ruthenium trichloride as starting materials according to the method described in Embodiment 1. The metal loading was 2.5 mass percent. The reaction was conducted according to the following procedure. Cellulose (Merck Inc., Avicel, 0.48 g) and distilled water (60 mL) were charged to an autoclave, the autoclave was closed, and 5 MPa of hydrogen was introduced at room temperature. At that time, the ratio of glucose units to the number of metal atoms was adjusted to a molar ratio of 110 (0.9 mol percent). The mixture was heated to 190° C. in an electric furnace while stirring with the motorized stirring vanes in the reactor (600 to 800 rpm) and reacted for 24 hours. After the reaction, the mixture was centrifugated and filtered to separate the solid from the supernatant aqueous solution. The product in the aqueous solution was analyzed by liquid chromatography (HPLC) and liquid chromatograph—mass spectrometry (LC-MS).

The results of the catalytic reaction are shown in Table 2. When non-treated cellulose was employed, the overall yield of sugar alcohols was 35.4 percent with Pt/Al$_2$O$_3$ (sorbitol (1): 27.7 percent, mannitol (2): 7.7 percent). In Embodiment 1, a stirrer was charged in the autoclave and stirring was conducted with a magnetic stirrer. However, in the present embodiment, stirring was conducted with stirring vanes, enhancing efficiency, to which the increased yield was attributed. FIG. 8 shows a typical liquid chromatogram of the products (cellulose pretreated with the ball milling, Ru/Al$_2$O$_3$ catalyst). In addition to sorbitol (retention time 19.3 minutes) and mannitol (retention time 15.5 minutes), there were also large peaks at retention times of 13.9 and 10.8 minutes, which were unidentified. However, based on LC-MS analysis, the peak at a retention time of 13.9 minutes was presumed to be didehyroxyhexitol (3) and the peak at a retention time of 10.8 minutes to be anhydrosorbitol (4). These are both sorbitol analogs in which two oxygen atoms or one water molecule, respectively, is eliminated from sorbitol. The structures of (1) to (4) are given below. For (3) and (4), the positions of the deoxygenation were undetermined.

[Chem. 2]

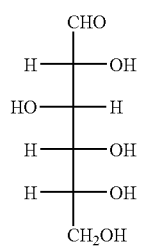

1

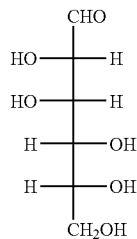

2

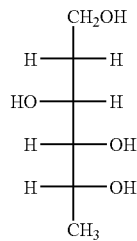

3

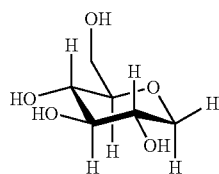

4

The total yield of the above four sugar alcohol analogs from untreated cellulose was 46.6 percent with Pt/A$_2$O$_3$. Under identical conditions, the total yield was 33.9 percent with Ru/Al$_2$O$_3$.

[Table 2]

TABLE 2

Sugar alcohol synthesis by degradation of pretreated cellulose

| Cellulose pretreatment | Catalyst | Yield (%) | | | | | |
|---|---|---|---|---|---|---|---|
| | | Sorbitol (1) | Mannitol (2) | Di-dehyroxy-hexitol (3) | Anhydro-sorbitol (4) | Total yield of sugar alcohols (1 + 2) | Total yield of sugar alcohol analogs (1 + 2 + 3 + 4) |
| None | Pt/Al$_2$O$_3$ | 27.7 | 7.7 | 6.2 | 5.0 | 35.4 | 46.6 |
| None | Ru/Al$_2$O$_3$ | 23.7 | 5.2 | 3.6 | 1.4 | 28.9 | 33.9 |
| Phosphoric acid | Pt/Al$_2$O$_3$ | 49.5 | 11.7 | 10.8 | 4.9 | 61.2 | 76.9 |
| Phosphoric acid | Ru/Al$_2$O$_3$ | 47.3 | 7.6 | 3.5 | 2.2 | 54.9 | 60.6 |
| Ball mill | Pt/HUSY (20) | 54.5 | 6.3 | 5.4 | 1.6 | 60.8 | 67.8 |
| Ball mill | Pt/Al$_2$O$_3$ | 41.0 | 10.4 | 7.2 | 12.0 | 51.4 | 70.6 |
| Ball mill | Ru/Al$_2$O$_3$ | 58.3 | 11.4 | 6.6 | 5.6 | 69.7 | 81.9 |

The yield increased when the cellulose was treated with phosphoric acid. With Pt/Al$_2$O$_3$ catalyst, the total yield of sugar alcohols was 61.2 percent, and the total yield of analogs was 76.9 percent. The yield also increased with phosphoric acid treatment for Ru/Al$_2$O$_3$ catalyst.

A rise in the yield was also observed for the ball milling treatment. With Pt/Al$_2$O$_3$ catalyst, the total yield of sugar alcohols was 51.4 percent, and the total yield of analogs was 70.6 percent. Similar results were obtained with Pt/HUSY (20). With Ru/Al$_2$O$_3$, the yield increased furthermore, to a total yield of sugar alcohols of 69.7 percent, and a total yield of analogs of 81.9 percent. Extremely high yields were thus achieved. Accordingly, the cellulose conversion was 80 percent or greater. The ratio of sorbitol to mannitol was 5.1.

As shown above, in the present embodiment, the yields of sugar alcohols and analogs are 70 percent or greater under the hydrogenation and degradation conditions in water with supported metal catalysts by using cellulose pretreated with phosphoric acid or by the ball milling treatment as the starting material.

INDUSTRIAL APPLICABILITY

The present invention is useful in the field of techniques of producing sugar alcohols (sorbitol and manitol) from cellulose resources.

Figure 1:
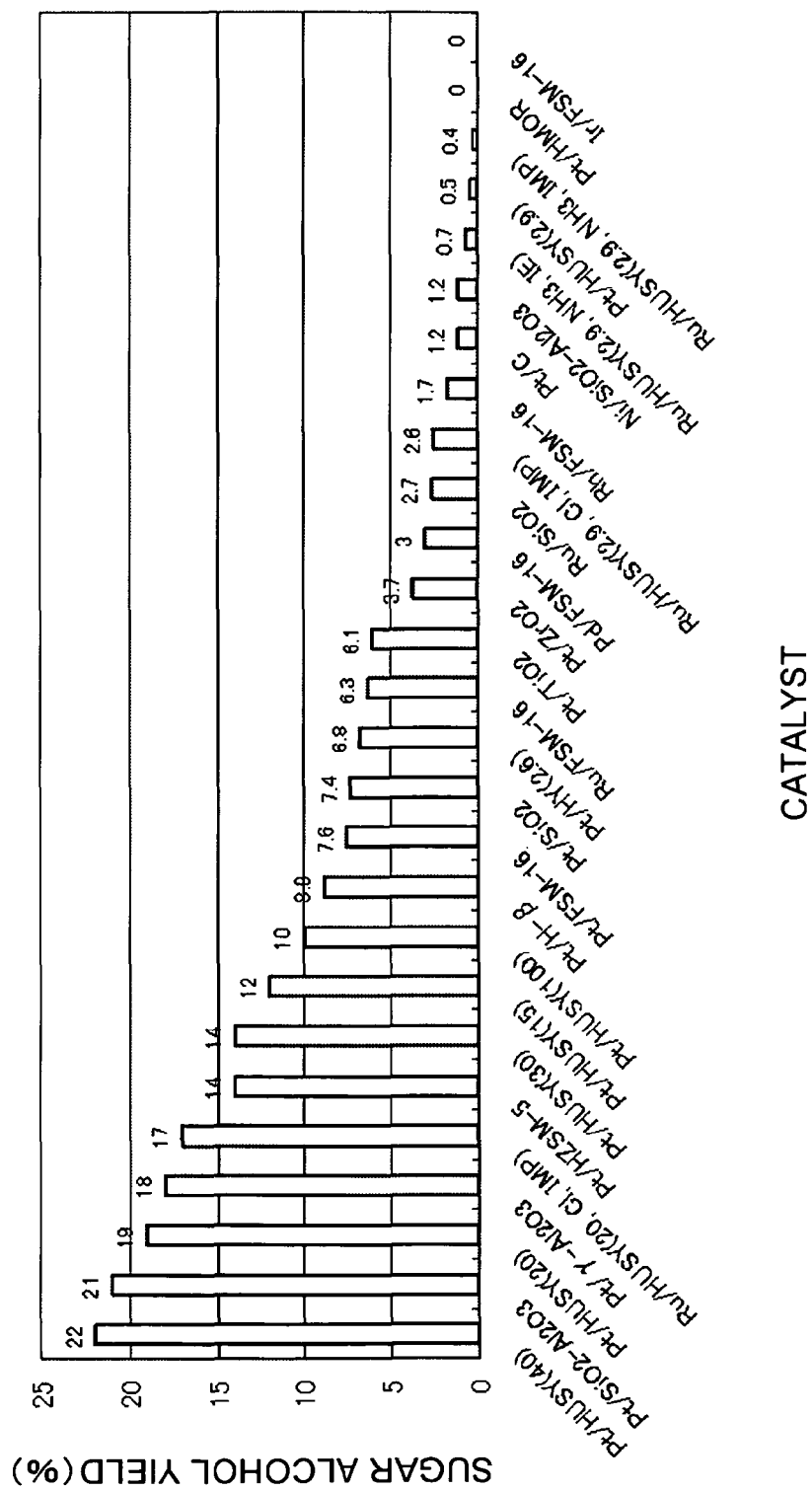
FIG. 1 shows the yield of sugar alcohols from cellulose with various catalysts.
Figure 2:
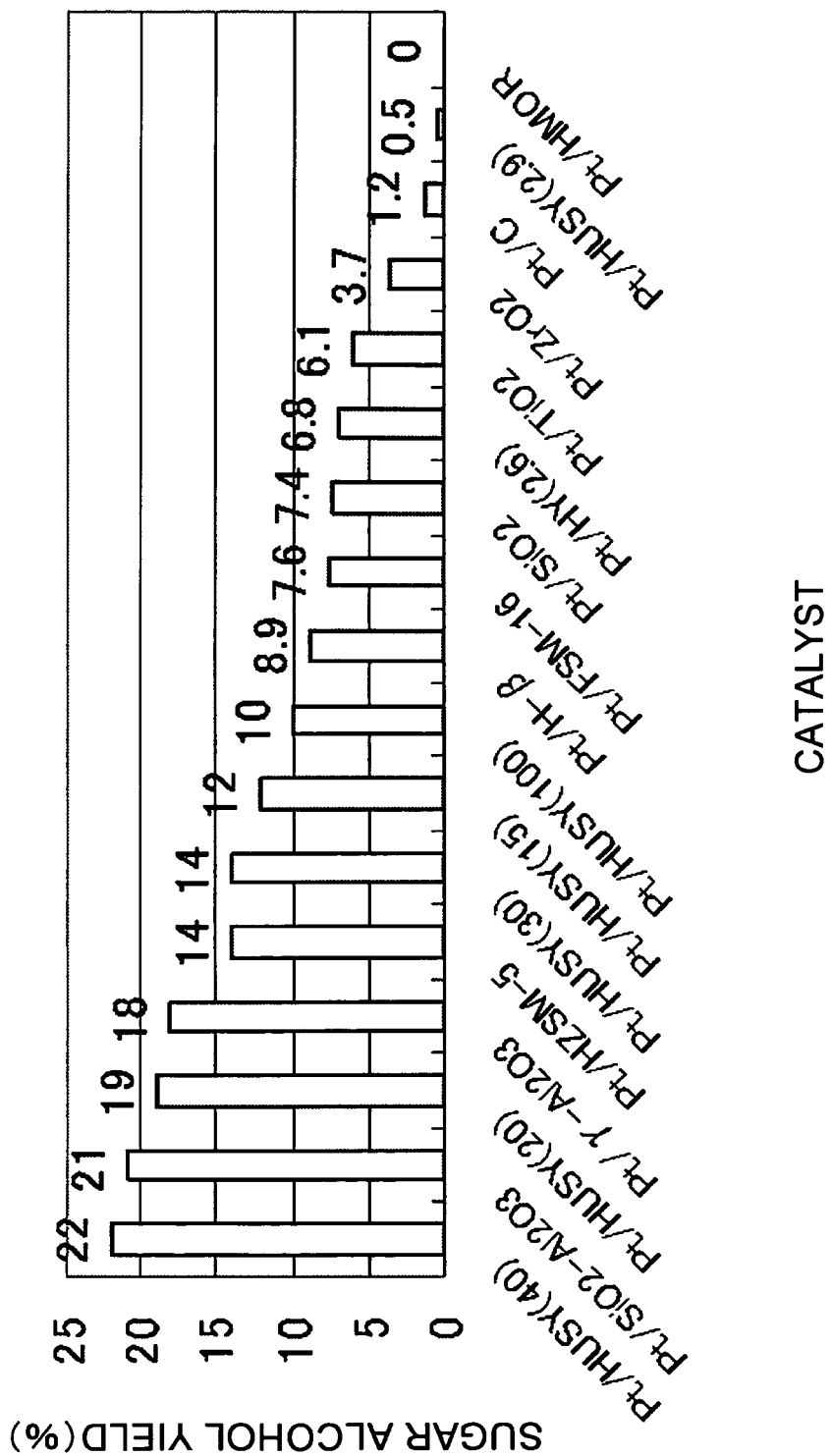
FIG. 2 shows the yield of sugar alcohols from cellulose with various Pt catalysts.
Figure 3:
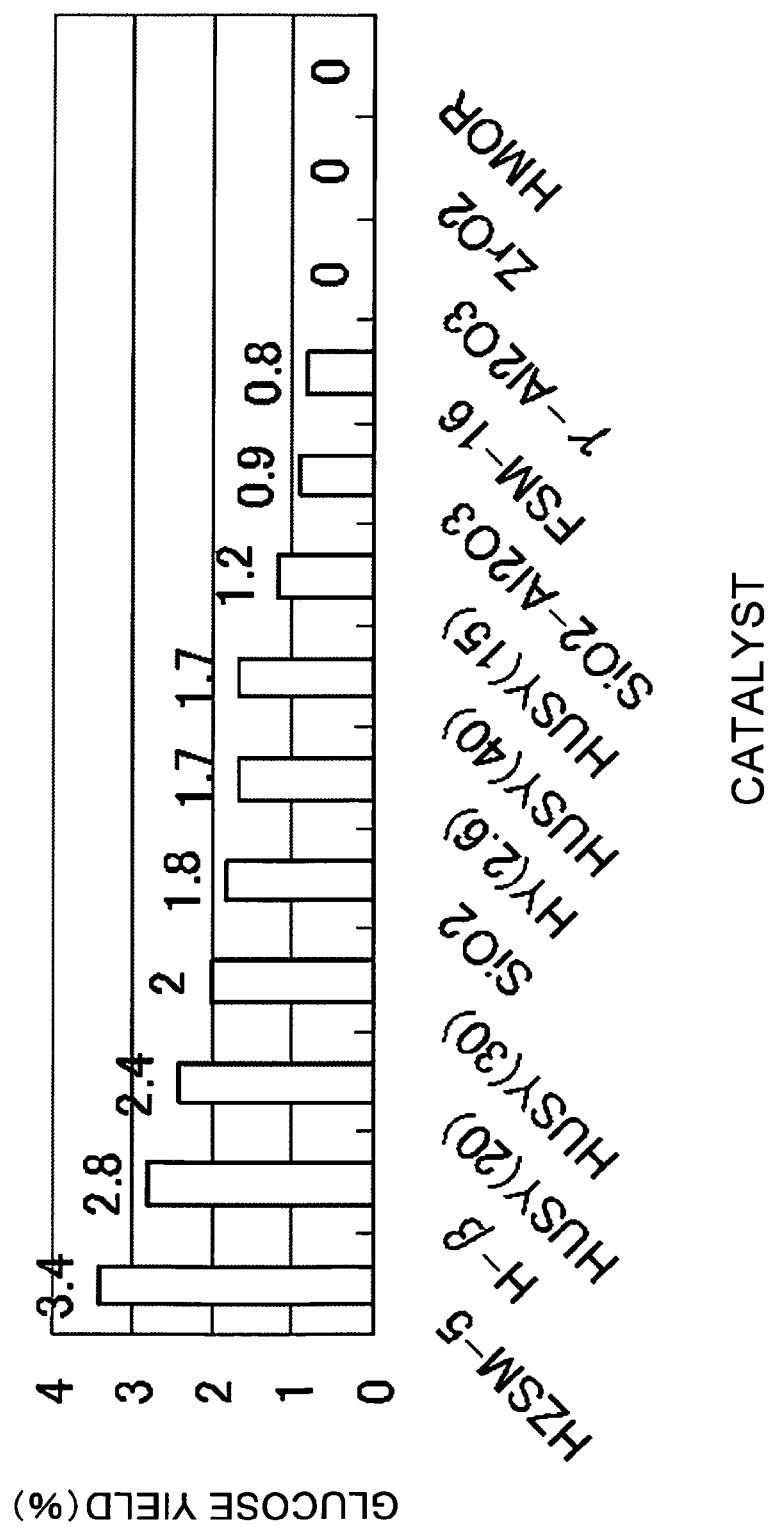
FIG. 3 shows the yield of glucose from cellulose with various supports.
Figure 4:
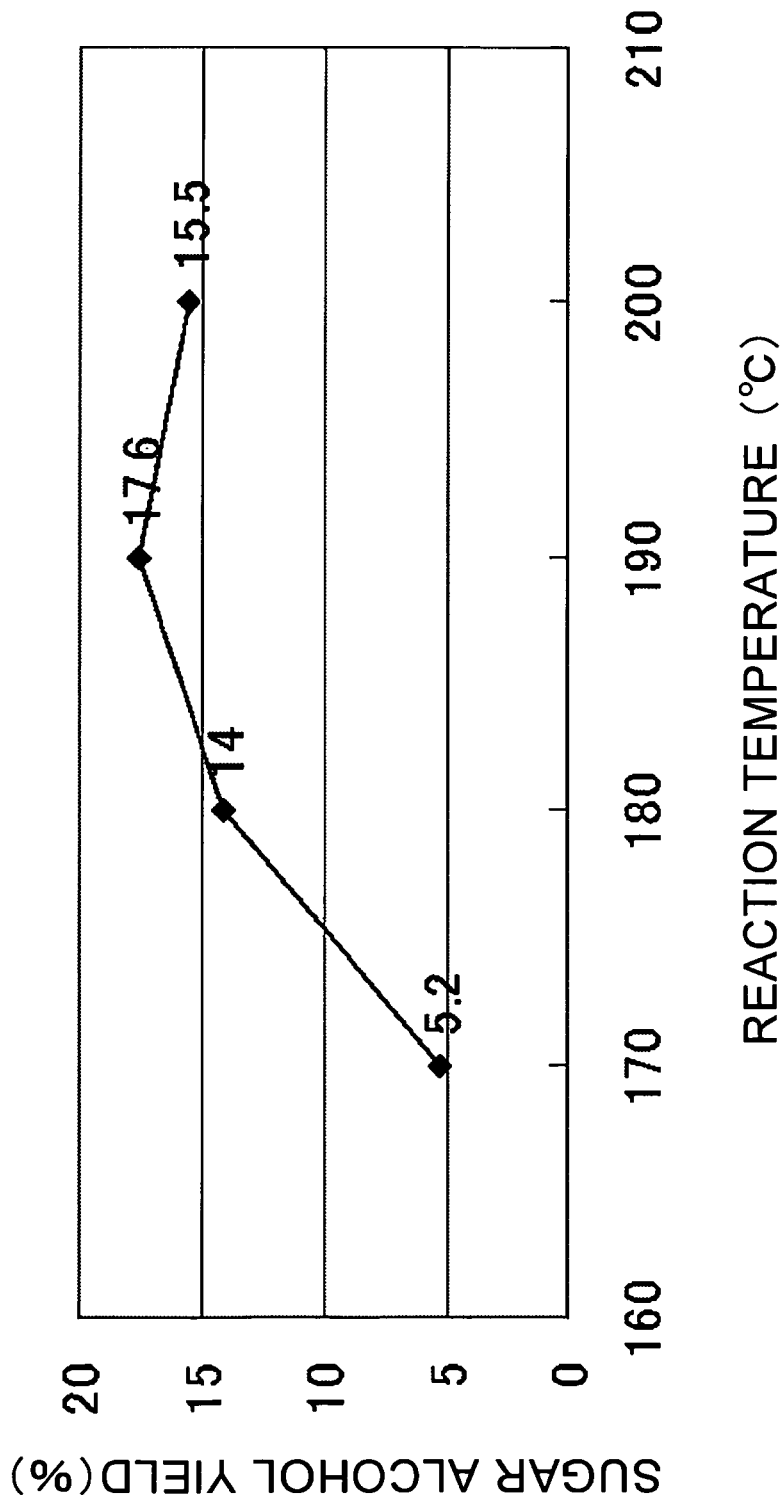
FIG. 4 shows the dependence of the sugar alcohol yield on the reaction temperature (catalyst: Pt/gamma-Al$_2$O$_3$).
Figure 5:
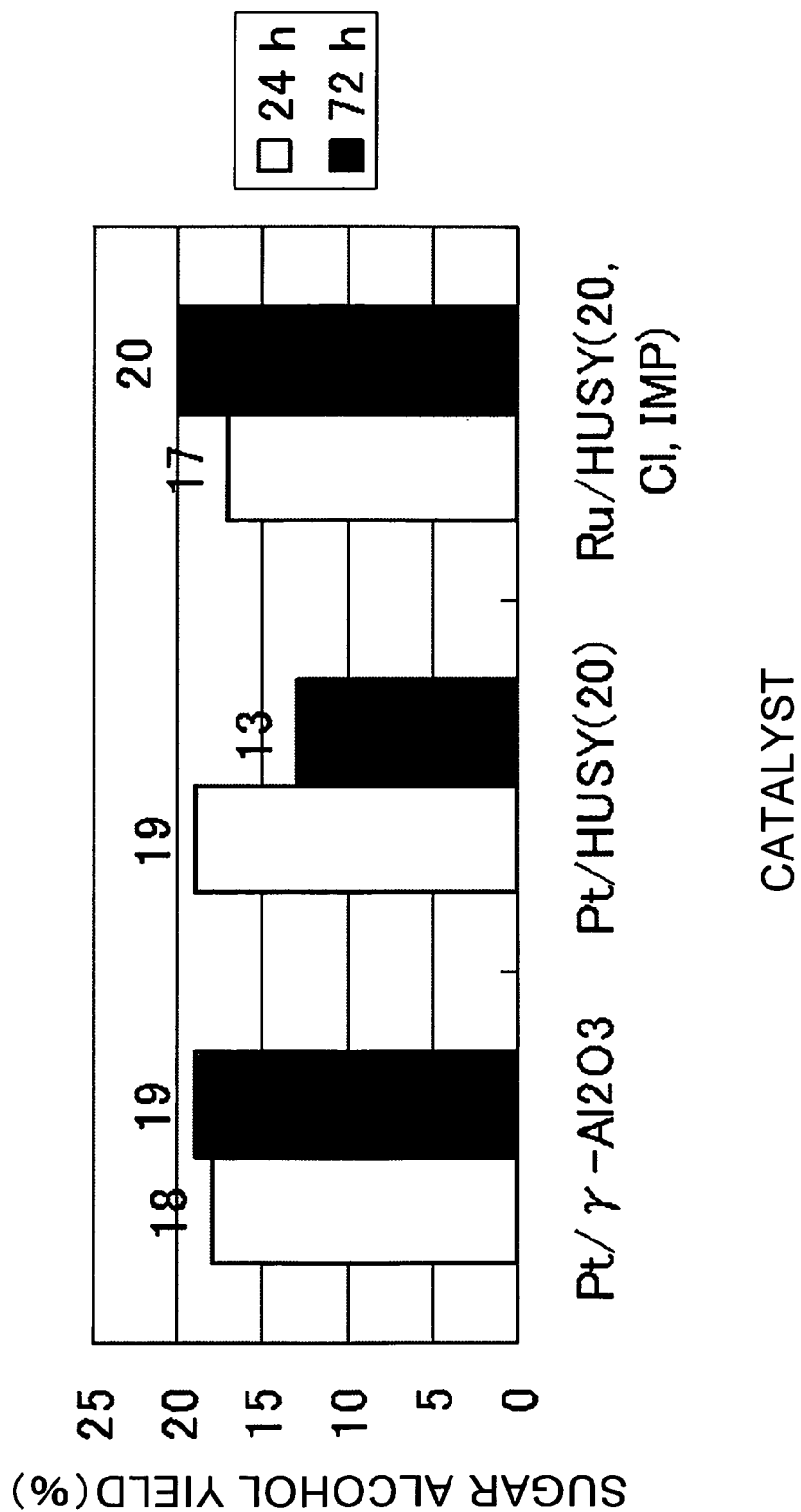
FIG. 5 shows the sugar alcohol yields in 24-hour and 72-hour reactions.
Figure 6:
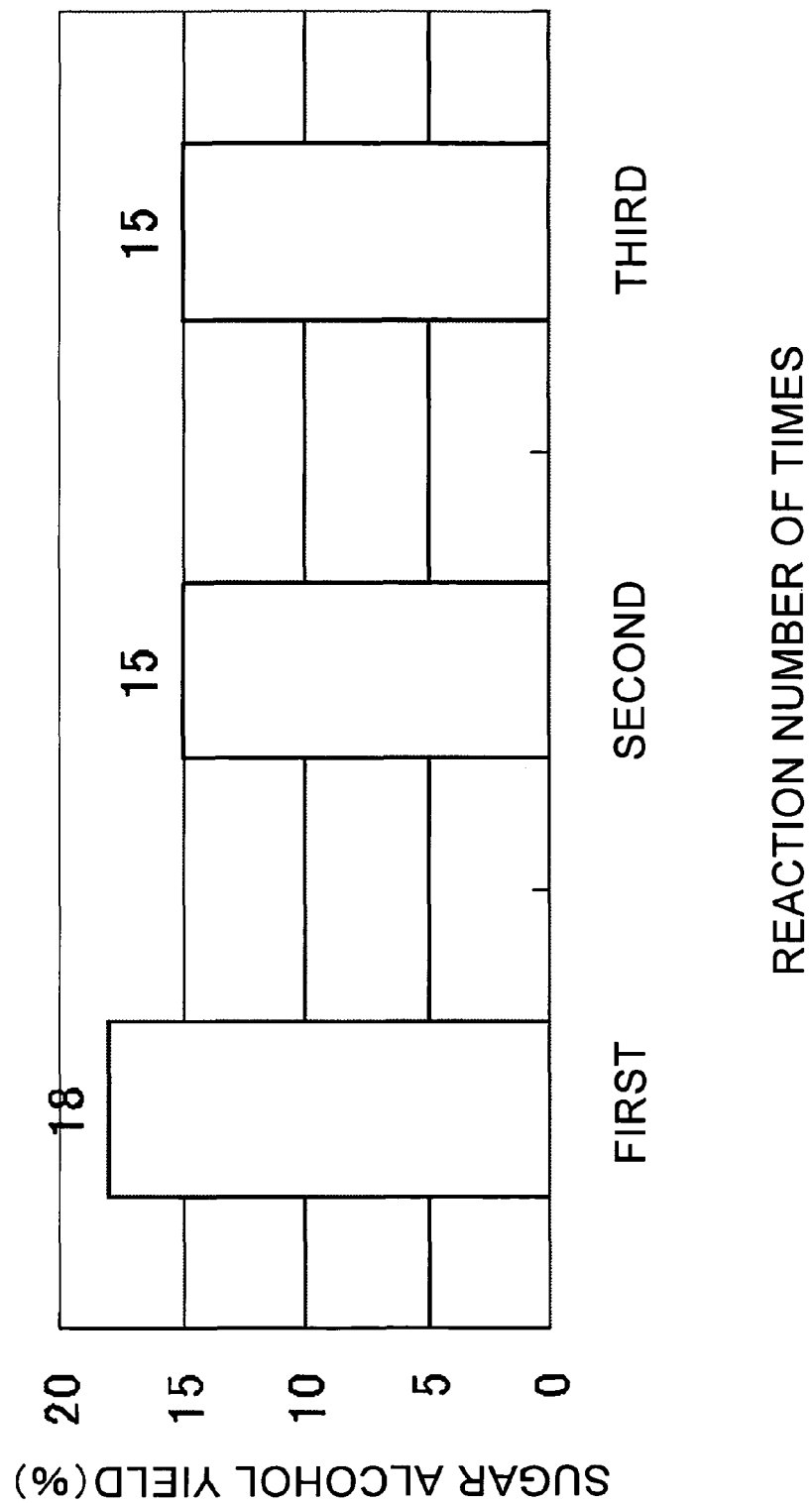
FIG. 6 shows a catalyst reuse test (catalyst: Pt/gamma-Al$_2$O$_3$).
Figure 7:
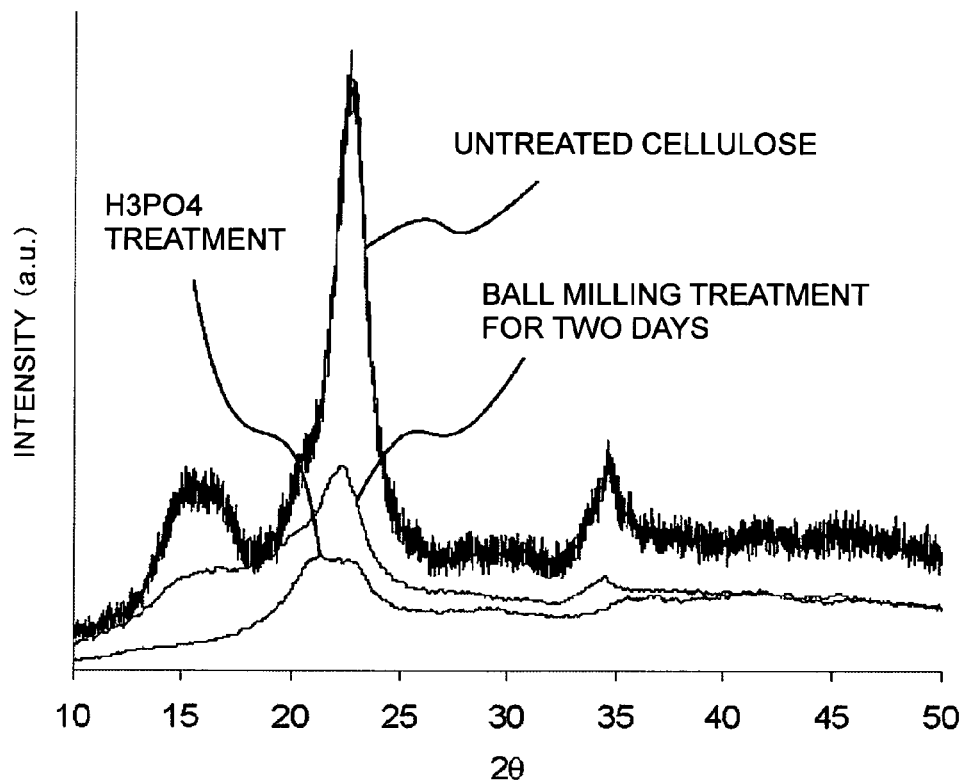
FIG. 7 shows the results of X-ray powder diffraction analysis of untreated cellulose and cellulose pretreated with phosphoric acid and ball milling.
Figure 8:
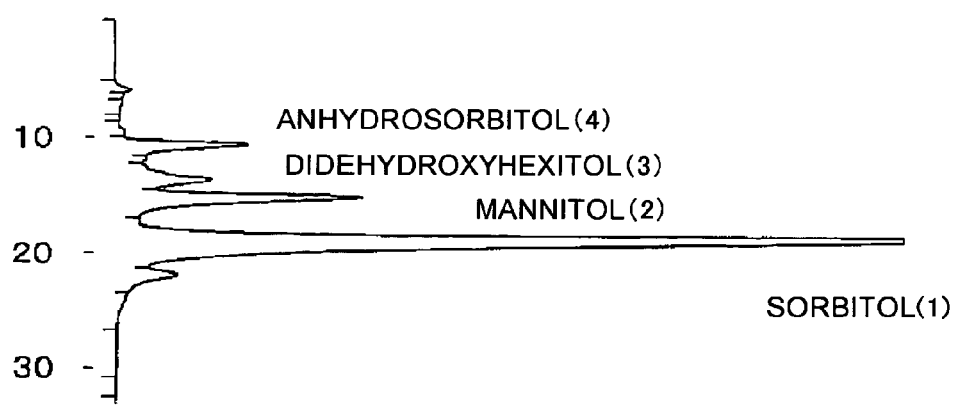
FIG. 8 shows a liquid chromatogram of the typical product (cellulose treated with ball milling, Ru/Al$_2$O$_3$ catalyst) obtained in Embodiment 7.

The invention claimed is:

1. In a method comprising cellulose hydrolysis in the presence of a catalyst, the improvement wherein the catalyst comprises (a) a solid support and (b) ruthenium supported on the solid support surface at a dispersion by carbon monoxide adsorption of 0.01 to 0.03.

2. A method of producing a sugar alcohol comprising hydrolyzing cellulose in a hydrogen-containing atmosphere with pressurization in the presence of a catalyst comprising (a) a solid support and (b) ruthenium supported on the solid support surface at a dispersion by carbon monoxide adsorption of 0.01 to 0.03 and reducing the cellulose-hydrolysis product.

* * * * *